US00PP28100P2

(12) United States Plant Patent
Horvath

(10) Patent No.: US PP28,100 P2
(45) Date of Patent: Jun. 13, 2017

(54) ***ALLIUM* HYBRID PLANT NAMED 'WINDY CITY'**

(50) Latin Name: ***Allium* hybrid**
Varietal Denomination: Windy City

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 141 days.

(21) Appl. No.: 14/545,846

(22) Filed: Jun. 29, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen Redden

(57) ABSTRACT

A new, distinct *Allium* hybrid plant as shown and described, characterized by dark green foliage in combination with purple-violet flowers, on semi-sterile plants.

1 Drawing Sheet

Figure 1:
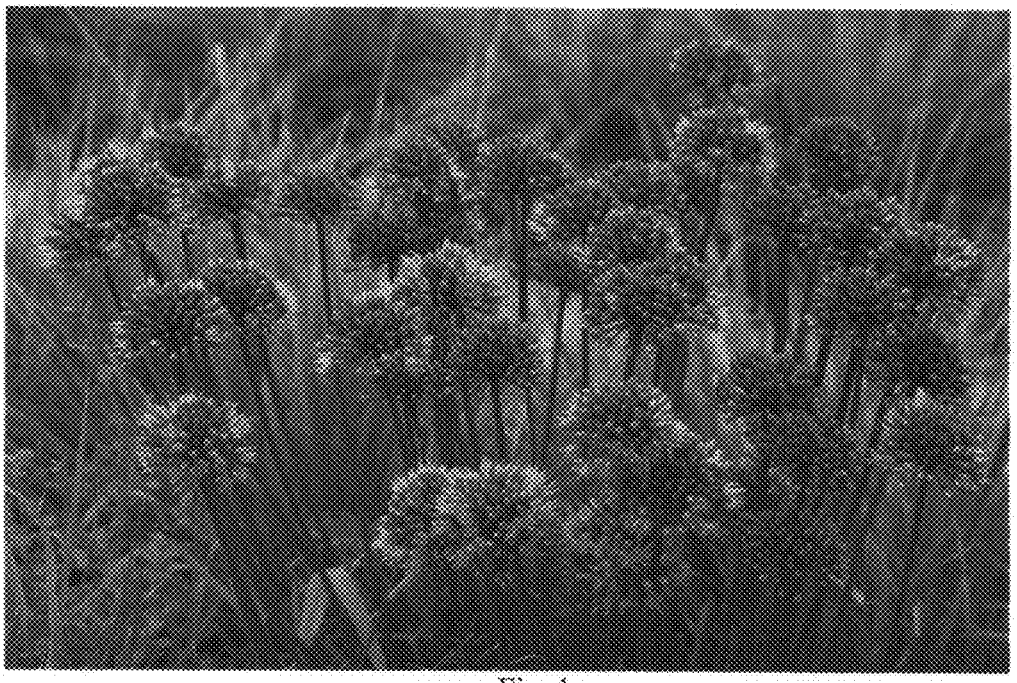

Latin name: *Allium* hybrid.
Cultivar name: 'Windy City'.

BACKGROUND OF THE INVENTION

The present invention relates to a new and distinct hybrid of *Allium* hybrid plant named 'Windy City' characterized by dark green foliage in combination with purple-violet flowers, on semi-sterile plants. The new *Allium* hybrid was the result of a breeding program taking place in Hebron, Ill. since 2010. 'Windy City' arose as a selection from seed sown from open pollination of unnamed plants of *Allium*. The exact parentage of *Allium* hybrid 'Windy City' is unknown, however the female or seed parent is believed to be *Allium* hybrid 'Summer Beauty', while the male pollen parent is unknown. The selection of the new plant was due to its' dark green foliage in combination with purple-violet flowers, on semi-sterile plants. Asexual division propagation has been the means of reproduction. The initial cutting and division propagation has taken place at a nursery in Hebron, Ill. in 2011. The new *Allium* has shown to be stable and identical in reproduction to the parent after dividing over 5000 plants from 2011 to 2015.

SUMMARY OF THE INVENTION

The new *Allium* hybrid plant named 'Windy City' characterized by dark green foliage in combination with purple-violet flowers, on semi-sterile plants, have been observed to be unique and stable.

Plants of the new *Allium* hybrid plant named 'Windy City' can be compared to the likely female or seed parent, *Allium* hybrid 'Summer Beauty', not patented. 1. The new plant height is typically 40-45 cm tall while *Allium* hybrid 'Summer Beauty' is typically 60 cm tall. 2. The new plant also has thinner dark green foliage RHS color 137 A measuring 10 mm wide, while *Allium* hybrid 'Summer Beauty', has green foliage RHS 137 C measuring 15 mm wide. 3. The new plant also has darker flowers RHS color N 81 A, while *Allium* 'Summer Beauty', has lighter pink flowers, RHS color not measured.

Plants of the new *Allium* hybrid can also be compared to plants of *Allium* hybrid 'Millenium', not patented. 1. The new plant height is typically 40-45 cm tall while *Allium* hybrid 'Millenium' is typically 50 cm tall. 2. The new plant also has thinner dark green foliage measuring 10 mm while *Allium* hybrid 'Millenium', has wider green foliage measuring 15 mm wide. 3. The new plant also is mostly sterile with very little seed set after flowering, while *Allium* hybrid 'Millenium', is fertile with heavy seed set after flowering.

DESCRIPTION OF PHOTOGRAPHS

FIG. 1. A blooming plant in July on a 2 year old plant in Hebron, Ill. USA.

Figure 2:
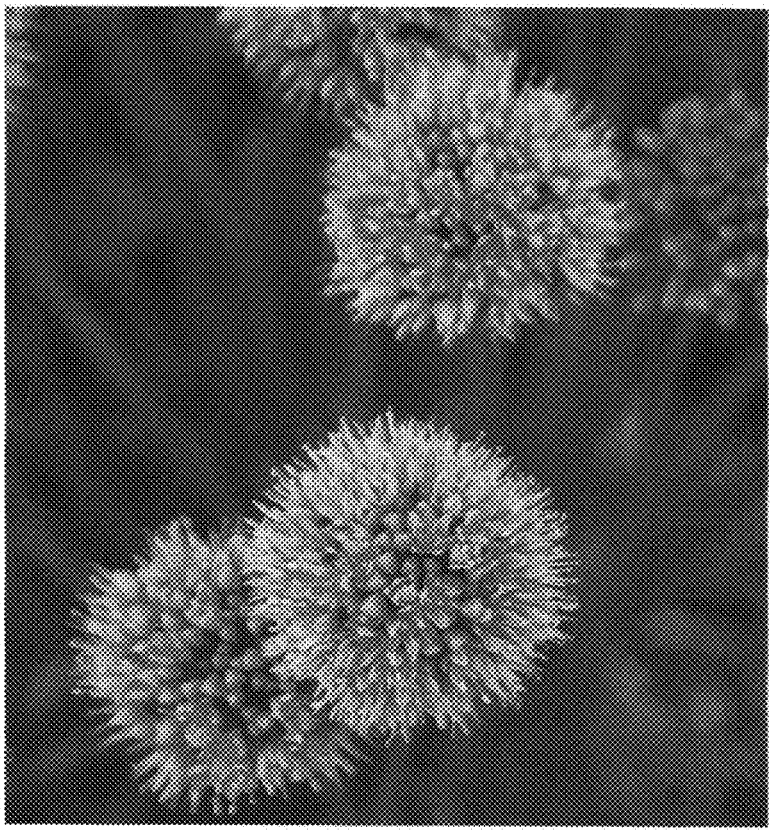

FIG. 2. Inflorescences in July on a 2 year old plant in Hebron, Ill. USA.

DETAILED BOTANICAL DESCRIPTION

In the following description, color references are made to The Royal Horticultural Society Colour Chart (2001). Plants used for the description were grown in a three gallon container for two years at a nursery in Hebron, Ill. Measurements and numerical values represent averages of typical plants.

Botanical classification: *Allium* hybrid cultivar 'Windy City'.

Parentage: Unknown.

Propagation: Vegetative division.

Plant description:

*Type*.—Herbaceous perennial. The overall habit of the new *Allium* hybrid is a basal tuft of dark green linear foliage arising from bulbous roots, with terminal purple-violet flower clusters in July, on semi-sterile plants.

*Hardiness*.—USDA zones 3-8.

*Plant height*.—40-45 cm.

*Plant width*.—45 cm.

Stem description:

*Stem shape*.—Round with ridges, solid.

*Stem size*.—Diameter — up to 10 mm at the widest by 5-6 mm at the thinnest.

*Stem length.*—40 cm.
*Internodes.*—None.
*Stem coloration.*—Stem color 139 A.
*Stem texture.*—Ridged, smooth, glabrous.
*Roots.*—Fibrous below the bulb, color 155 C.
*Bulb.*—Size — 12-15 mm wide at the base, 7 mm wide at the top where the foliage begins, 25 mm in length, color: ranges from 155 C to 145 B.

Foliage description:
*Shape.*—Linear.
*Arrangement.*—Basal, alternate.
*Leaf blade size.*—Length: up to 30 cm, Width: 6 mm.
*Margins.*—Entire.
*Petiole.*—None.
*Leaf apex.*—Acute.
*Leaf base.*—Attenuate.
*Leaf quantity.*—An average of 6 per stem.
*Texture.*—Upper and lower surfaces: smooth, glabrous.
*Adaxial and abaxial leaf color description.*—137 A.
*Venation pattern.*—Parallel.
*Venation color.*—Upper 137 A, lower 137 A.

Flower description:
*Inflorescence type.*—Umbel, round, held on a leafless stalk.
*Umbel size.*—Length: 4-4.5 cm tall, width: 5 cm.
*Peduncle size and color.*—Length: 15 cm, diameter: 2 mm, color — 139 A.
*Peduncle texture.*—Smooth, glabrous.
*Pedicel size and color.*—Length: 15 mm, diameter: less than 1 mm, color — 137 A.
*Flower bud.*—Size: length: 23 mm, diameter: 40-45 mm.
*Flower bud surface.*—Smooth, glabrous.
*Flower bud shape.*—Ovoid, tubular, constricted at the base.
*Flower bud color.*—Between N 81 B and C.
*Corolla description.*—3 petals unfused, constricted at the base.
*Petal apex.*—Entire, acute.
*Petal base.*—Unfused.
*Petal margin.*—Entire.
*Petal texture.*—Outer surface: smooth, inside surface: smooth.
*Petal color.*—Outer surface — is color N81 A, inside surface — color is N81 B.
*Calyx shape.*—Stellate.
*Calyx size.*—Length: 5 mm, Width: 2 mm.
*Calyx color.*—N 81 A.
*Sepal quantity and arrangement.*—3, unfused.
*Sepal size.*—Length: 5 mm, diameter: 2 mm at base coming to a point.
*Sepal shape.*—Lanceolate, apex: acute, base: cuneate, margin: entire.
*Sepal texture.*—Upper and lower surfaces: smooth, glabrous.
*Sepal color.*—Adaxial color N81 A, Abaxial color N81 A.
*Flower type and shape.*—Bowl, comprised of 3 sepals and 3 petals.
*Flower color.*—N81 A outside, N81 A inside.
*Flower size.*—Length: 10 mm, width: 10 mm.
*Flower number.*—125 per umbel, 5000 per plant with up to 50 flowering stems.
*Bloom period and duration.*—3-4 weeks the beginning of July in Hebron, Ill.
*Flower longevity and duration on the plant.*—Approximately 3 weeks.
*Flower longevity and duration cut.*—Not measured.
*Scent.*—None.

Reproductive organs:
*Stamen.*—Quantity: 6, length: 8 mm, diameter: 1 mm at the base getting thinner toward the tip.
*Anther.*—Quantity: 6, length: 2 mm, diameter: 1 mm.
*Anther shape.*—Oval, color not measured.
*Filament.*—Cream colored at tip near anther, pink at the base.
*Pollen.*—Sparse, color: creamy yellow, RHS color not measured.
*Pistil.*—Number: 1, length: 9 mm, width: 3 mm, color — between N81 C and D.
*Stigma shape.*—Conical, color — N81 A.
*Style.*—Number: 1, length: 9 mm, width 3 mm.
*Ovaries.*—Made of 3 carpels, length: 3 mm, width: 3 mm.
*Fruit.*—Capsule more or less round, 2-3 mm long, 2-3 mm wide, glabrous, color black 202 A.

Disease resistance: Resistance to diseases common to *Allium* has not been observed on plants grown under nursery conditions.

I claim:

1. A new, distinct *Allium* hybrid plant as shown and described, characterized by dark green foliage in combination with purple-violet flowers, on semi-sterile plants.

* * * * *